United States Patent [19]
Allocca

[11] Patent Number: 5,939,076
[45] Date of Patent: Aug. 17, 1999

[54] COMPOSITION AND METHOD FOR TREATING OR ALLEVIATING MIGRAINE HEADACHES

[75] Inventor: John A. Allocca, Northport, N.Y.

[73] Assignee: Allocca Techical, Inc., Northport, N.Y.

[21] Appl. No.: 08/968,358

[22] Filed: Nov. 12, 1997

[51] Int. Cl.⁶ .............................. A61K 9/00; A61K 9/48
[52] U.S. Cl. ..................... 424/400; 424/451; 424/456; 514/962; 514/649; 514/415
[58] Field of Search ..................... 424/400, 451, 424/456; 514/962, 649, 415

[56] References Cited

U.S. PATENT DOCUMENTS

| | | |
|---|---|---|
| 4,029,807 | 6/1977 | Roldan et al. . |
| 4,299,838 | 11/1981 | Durlach . |
| 4,377,595 | 3/1983 | Wurtman . |
| 4,472,387 | 9/1984 | Laruelle et al. . |
| 4,596,807 | 6/1986 | Crosby . |
| 4,639,465 | 1/1987 | Pollack et al. . |
| 4,650,789 | 3/1987 | Pollack . |
| 4,698,342 | 10/1987 | Crosby . |
| 4,772,591 | 9/1988 | Meisner . |
| 4,833,154 | 5/1989 | Jean-Louis et al. . |
| 4,853,377 | 8/1989 | Pollack . |
| 4,897,380 | 1/1990 | Pollack et al. . |
| 5,189,064 | 2/1993 | Blum et al. . |
| 5,250,529 | 10/1993 | Theoharides . |
| 5,470,846 | 11/1995 | Sandyk . |

FOREIGN PATENT DOCUMENTS 2 113 546   8/1983   United Kingdom .

*Primary Examiner*—Thurman K. Page
*Assistant Examiner*—Brian K. Seidleck
*Attorney, Agent, or Firm*—Ohlandt, Greeley, Ruggiero & Perle, L.L.P.

[57] ABSTRACT

A method of preventing or alleviating a migraine headache in a patient subject to migraine headaches comprises administering to the patient daily, for an effective period of time, a daily effective amount of a dietary supplementation of serotonin and norepinephrine precursors to increase the level of serotonin and norepinephrine in the patient.

22 Claims, No Drawings

COMPOSITION AND METHOD FOR TREATING OR ALLEVIATING MIGRAINE HEADACHES

FIELD OF THE INVENTION

This invention relates to a method for preventing or alleviating migraine headaches and compositions therefor. More particularly, this invention relates to compositions and methods for preventing or alleviating migraine headaches through vasomotor control.

BACKGROUND OF THE INVENTION

Migraine headaches are the most severe or intensive type of headaches and affect approximately fifteen percent of the population. This disdorder is highly disruptive of the life of a sufferer thereof and also results in a very significant amount of lost work time. Moreover, there has been no really effective way to prevent the onset of such migraine headaches.

After the prodromal stage, the migraine attack has two main phases, namely the aural phase and the acute painful headache phase. Several sympions occur during the aural phase, such as visual scotomata (absence of vision within the visual field), spots, scintillating (flashing) visual scotomata, and other visual disturbances. Additionally, the migraine sufferer may become tired and possibly faint. As these symptoms of the aural phase slowly disappear, a throbbing hemi-cranial pain develops, either on one side, the front or the rear of the head. Other symptoms such as nausea or diarrhea may occur during a severe migraine headache. Migraine headaches develop suddenly and reach an intense level quickly.

Heretofore, a wide variety of pharmacological agents have been employed in attempts to treat a person suffering from migraine headaches. For the most part, these pharmacological agents have been employed to treat the symptoms of a migraine headache after the onset or occurrence of the acute painful headache phase. Among the many types of pharmacological agents suggested for treatment of migraine headaches are antihistamines in combination with analgesics, vasodialators such as papaverine, beta-andrenergic blockers such as propranolol, nadolol, timolol and antenolol, calcium channel antagonists, and various phenothiazines.

Extracranial vasoconstrictors, such as ergot alkaloids, for example, ergotamine and sumatriptan, have also been employed since it has been considered that increased levels of norepinephrine, seratonin, bradykinin and substance P were considered to be the endogenous pain-producing compounds in combination with stretching due to vasoconstriction and vasodilation resulting as a reflex action to a variety of stimuli, such as intense light, noise, anxiety, exertion, cold, heat, hormones, and certain foods.

Recently in U.S. Pat. No. 5,250,529 it is suggested to treat migraine patients with a mast cell degranulation blocking agent, e.g. hydroxyzine or ketotifen, alone or in combination with a central nervous system stimulant, e.g. caffeine, just prior to or during the prodomol stage of the migraine so as to inhibit the release from mast cells of the vasoactive and nociceptive compounds involved in precipitating the migraine headache. This treatment is proposed based on the assumption that increased levels of norepinephrine, serotonin, bradykinin and substance P, as well as products of tissue anoxia are considered to be the endogenous pain-producing compounds. However, even this suggested treatment has not led to a successful means to prevent development of a migraine headache.

It is therefor an object of this invention to provide a method of preventing and alleviating migraine headaches in patients subject to such migraine headaches, and to compositions or dietary regimens to accomplish same.

BRIEF SUMMARY OF THE INVENTION

It has been discovered that loss of serotonin and norepinephrine or reduction of levels of serotonin and norepinephrine in the brain below certain levels causes a loss of vasomotor control by the hypothalmus of various circulatory paths in the brain. It is this loss of vasomotor control that causes the arteries to dilate (lose ability to constrict) and develop a migraine headache. That is, migraine is a cerebral vascular disorder in which vasoconstriction is experienced in the pre-headache phase and vasodilation and associated pain in the headache phase. When the levels of neurotransmitters serotonin and norepinephrine fall below a certain level, a person loses vasomotor control. Many factors have been found to lead to loss of neurotransmitters, including but not limited to allergic reactions (especially to foods), inflammation, poor absorption of precursors into the brain and poor metabolism in the brain.

In accordance with this invention a daily supplementation of precursors for the neurotransmitters serotonin and norepinephrine is provided in order to increase the average daily levels of these neurotransmitters and thereby prevent or inhibit a drop in sero-tonin and norepinephrine levels in the brain to levels causing loss of vasomotor control and in that manner avoid the onset of a migraine headache. The precursors may be administered with one or more of other ancillary agents such as bioflavanoids, antioxidants, methyl donors, anti-allergic substances, cell membrane support substances, sources of copper, calcium, magnesium and niacin, vitamin C, vitamin B6, choline and folic acid.

DETAILED DESCRIPTION OF THE INVENTION

In accordance with this invention patients (potential migraine sufferers) are administered daily supplements of precursors for the neurotransmitters serotonin and norepinephrine to maintain or elevate brain levels of these neurotransmitters so that the levels thereof are prevented or inhibited from falling below the level causing loss of vasomotor control by the hypothalmus of various circulatory paths to the brain.

The daily supplementation of precursors for serotonin and norepinephrine comprises administering, for an effective daily period, an effective amount of L-tryptophan or L-5-hydroxytryptophan as the precursors for serotonin and L-tyrosine as the precursor for norepinephrine. The serotonin precursor is generally taken at bedtime, generally about 3 to 4 hours after the last meal of the day and is most preferably taken with cold fruit juice. The norepinephrine precursor is taken during the day, generally with food.

It has been discovered that taking these daily supplements of precursors for serotonin and norepinephrine enable the migraine sufferer to maintain sufficient brain levels of serotonin and norepinephrine to avoid loss of vasomotor control and avoid the onset of a migraine headache.

While the daily amount of precursors required to maintain or elevate brain levels of serotonin and norepinephrine will vary from patient to patient, it has been found that generally about 900 mg L-tryptophan or 180 mg L-5-hydroxytryptophan and about 800 mg L-tyrosine are generally sufficient to accomplish the desired purpose and avoid loss of vasomotor control in the patients.

It is also desirable that the daily supplement of serotonin precursor include an effective amount of at least one carbohydrate, such as fructose, corn starch or dextrose, to stimulate the production of insulin to facilitate absorption of the serotonin precursor across the blood brain barrier. It is also desirable that the daily supplement of serotonin precursor include an effective amount of niacin, such as inositol hexanicotinate, to insure that the serotonin precursor is not converted to niacin instead of serotonin. The niacin also is useful for vasomotor control. Additionally, it is desirable to include an effective amount of pyridoxine HCl (vitamin B6) to inhibit tryptophan oxygenase which metabolizes tryptophan.

It is also desirable for the daily supplement of precursors for serotonin and norepinephrine to include therewith effective amounts of various other components. These other components can be present with either the daily supplement of the serotonin precursor or the norepinephrine precursor or with both supplements. Among these other components are the following components.

An effective amount of vitamin C, an antioxidant, and proanthocyanidins, an antioxidant and antihistimine, are generally included to help reduce allergic reactions causing loss of serotonin and norepinephrine. The vitamin C is also helpful in the production of norepinephrine from tyrosine and the proanthocyanidins as a collagen protector to hold together the cells of the blood vessel wall and blood brain barrier. Preferably the vitamin C source, e.g. calcium ascorbate, is at least present in the norepinephrine supplement and generally is present in both daily precursor supplements, and the proanthocyanidins to preferably present with the norepinephrine precursor supplement.

An effective amount of a bioflavanoid, such as quercitin, rutin or hexperidin, is included to strengthen outer cell membranes and help stabilize the cell surface and to stabilize the cell walls of basophils and mast cells, so they will not burst easily and release histimine and other inflammatory chemicals in the patient. Preferably, the bioflavanoid is quercitin and the bioflavanoid is preferably included with the norepinephrine precursor supplement.

An effective amount of calcium, e.g. as calcium citrate, and magnesium, e.g. magnesium citrate or aspartate, is included for normal nerve transmission. Additionally, the magnesium is helpful for vasomotor control. Both the calcium and magnesium are preferably included with the norepinephrine supplement and more preferably with both precursor supplements.

An effective amount of copper, e.g. as copper sebacate, is helpful in the production of norepinephrine from tyrosine and is included in the norepinephrine precursor supplement.

Folic acid, which facilitates the production of neurotransmitters, is generally included in an effective amount and preferably with the norepinephrine precursor supplement.

Generally an effective amount of choline, e.g. as choline citrate, is included as a precursor for the neurotransmitter acetylcholine and as an aid to increase uptake of magnesium. The choline is preferably included with the serotonin precursor supplement.

An effective amount of a methyl donor, e.g. dimethylglycine, is generally included and is preferably included with the serotonin precursor supplement.

It will be appreciated that any number of other various optional nutritional or other components may be incorporated into the daily precursor supplements of this invention.

It will be appreciated that the daily supplements of serotonin and norepinephrine precursors can be formulated in a wide variety of formulations, as described hereinbefore, and that the following formulations are merely exemplary of such supplement formulation. In addition to taking the daily supplements of serotonin and norepinephrine precursors, the patients also preferably adjust or alter their dietary regime to avoid, as much as possible, an allergic reaction to food so as to inhibit or present release of histamine and other inflammatory chemicals.

Examples 1 to 4 are examples of suitable daily serotonin precursor supplement formulations and Examples 5 and 6 are examples of suitable daily norepinephrine precursor supplement formulations.

EXAMPLE 1

Magnesium aspartate (220 mg magnesium)—1,100 mg

Dextrose, anhydrous—500 mg

L-5-hydroxytryptophan—180 mg

Calcium ascorbate (140 mg vitamin C)—175 mg

Inositol hexanicotinate (78.6 mg of niacin)—100 mg

Pyridoxine HCl—170 mg

Choline citrate (35 mg choline)—100 mg

Dimethylglycine HCl—100 mg

Each of the above ingredients is placed in a mortar and ground to a fine powder with a pestle.

This formulation can be taken as a powder mixed with cold fruit juice, but the powder is generally placed into 3 suitable capsules and taken with cold fruit juice at bedtime, about 3–4 hours after the last daily meal. It is also possible to take additional dosages between meals on an empty stomach, if desirable.

EXAMPLE 2

Magnesium aspartate (220 mg magnesium)—1,100 mg

Dextrose, anhydrous—500 mg

Tryptophan—1,000 mg

Calcium ascorbate (140 mg vitamin C)—175 mg

Inositol hexanicotinate (132.6 mg of niacin)—170 mg

Pyridoxine HCl—170 mg

Choline citrate (35 mg choline)—100 mg

Dimethylglycine HCl—100 mg

The ingredients are formed into a powder and optionally placed into 3 capsules and taken in the manner described in Example 1.

EXAMPLE 3

Fructose—4,400 mg

Corn starch—3,500 mg

L-tryptophan—900 mg

Calcium ascorbate (200 mg of vitamin C)—250 mg

Inositol hexanicotinate (156 mg of niacin)—200 mg

Pyridoxine HCL—200 mg

The ingredients are formed into a powder and optionally placed into 3 capsules and taken in the manner described in Example 1.

EXAMPLE 4

Fructose—900 mg

Corn starch—500 mg

L-5-hydroxytryptophan—180 mg

Calcium ascorbate (140 mg of vitamin C)—175 mg

Inositol hexanicotinate (132.6 mg of niacin)—170 mg

Pyridoxine HCL—170 mg

This daily supplement is formed and taken in the same manner as described in Example 1.

EXAMPLE 5

Quercetin—500 mg

L-tyrosine—800 mg

Calcium ascorbate (160 mg vitamin C)—200 mg

Magnesium aspartate (40 mg magnesium)—200 mg

Calcium citrate (44 mg calcium)—200 mg

Proanthocyanidins (grape seed extract)—100 mg

Copper sebacate (4 mg copper)—20 mg

Folic acid—400 mcg

Each of the above ingredients is placed in a mortar and ground to a fine powder with a pestle. This formulation can be taken as a powder mixed with a suitable fluid, but the powder is generally placed into 3 suitable capsules and taken with a suitable fluid with or without food during the day.

EXAMPLE 6

Quercetin—600 mg

L-tyrosine—500 mg

Calcium ascorbate (400 mg vitamin C)—500 mg

Magnesium citrate (80 mg magnesium)—500 mg

Calcium citrate (44 mg calcium)—200 mg

Proanthocyanidins (grape seed extract)—40 mg

Copper sebacate—(4 mg copper)—20 mg

Folic acid—400 mcg

The ingredients are formed into a powder and optionally placed in capsules and taken in the manner described in Example 5.

EXAMPLE 7

A male patient, age 48, had a forty year history of migraine headaches with aura occurring at approximately once to twice per week intervals. The patient was unable to obtain relief or prevention of the migraine headaches from any of the presently available pharmaceutical drugs. Adjustment of the patient's diet produced only a slight but not significant reduction in migraine frequency. The patient began taking the daily dietary supplement of serotonin and norepinephrine precursors of this invention in November 1996 along with diet adjustment. The patient has not experienced a migraine headache since that time.

EXAMPLE 8

A female patient, age 34, had a fifteen year history of migraine headaches with aura occurring at approximately once per week intervals. This patient was unable to obtain relief or prevention of the migraine headaches from any presently available pharmaceutical drugs. An adjustment in diet of the patient produced only a slight, but not significant, reduction in migraine frequency. The patient began taking the daily dietary supplement of serotonin and norepinephrine precursors of this invention in December 1996 along with the dietary adjustment. The patient has not experienced a migraine headache since that time.

EXAMPLE 9

A female patient, age 67, had a fifty year history of migraine headaches with aura occurring at intervals of approximately one to three times per week. This patient had become disabled from migraine headaches approximately twenty years ago. The patient was unable to obtain relief or prevention of the migraine headaches from any of the available pharmaceutical drugs. An adjustment of the patient's diet produced only a slight, but not significant, reduction in migraine frequency. This patient began taking the daily dietary supplement of serotonin and norepinephrine precursors of this invention in June of 1997 along with the adjusted diet. The patient has not experienced a migraine headache since that time.

In Examples 7 to 9 the patients ingested approximately 180 mg L-5-hydroxytryptophan and from about 500 to 800 mg L-tyrosine daily in the formulation of Example 1 and 5 or 6.

With the foregoing description of this invention, those skilled in the art will appreciate that modifications may be made to this invention without departing from the true spirit and scope thereof. Therefore, it is not intended that this invention be limited to the specific embodiments illustrated and described.

What is claimed is:

1. A method of treating or alleviating a migraine headache in a patient subject to migraine headaches, said method comprising administering to said patient daily, for an effective period of time, a daily effective amount of a dietary supplementation to provide the serotonin precursor L-tryptoghan or L-5-hydroxytryptophan and the norepinephrine precursor L-tyrosine sufficient to increase brain levels of serotonin and norepinephrine in the patient to avoid loss of vasomotor control of circulatory paths to the brain and thereby avoid the onset of or alleviate a migraine headache.

2. The method according to claim 1 wherein the dietary supplementation includes a bioflavanoid.

3. The method according to claim 2 wherein the bioflavanoid is selected from the group consisting of quercetin, rutin and hexperidin.

4. The method according to claim 3 wherein the bioflavanoid is quercetin.

5. The method according to claim 4 wherein a first formulation containing the L-tryptophan or 5-hydroxytryptophan is administered to the patient daily at least about 3 hours after the last meal taken in the day by the patient, and the second formulation containing the L-tyrosine is administered to the patient during the day, optionally with food.

6. The method according to claim 5 wherein the second formulation is administered to the patient in a daily dosage taken around the time food is ingested by the patient.

7. The method according to claim 6 wherein the first formulation is taken at bedtime as capsules of said first formulation and taken with cold juice, and said second formulation is taken in capsules dosage of said second formulation and taken at mealtime.

8. The method according to claim 5 wherein each of the first and second formulations additionally comprise one or more of the following components: a source of magnesium, a source of calcium, a source of copper, a source of niacin, a source of vitamin C, a source of vitamin B6, a source of choline, a source of methyl donor, folic acid, and proanthocyanidins.

9. The method according to claim 5 wherein the first formulation comprises:

Magnesium aspartate (220 mg magnesium)—1,100 mg

Dextrose, anhydrous—500 mg

L-5-hydroxytryptophan—180 mg

Calcium ascorbate (140 mg vitamin C)—175 mg
Inositol hexanicotinate (78.6 mg of niacin)—100 mg
Pyridoxine HCl—170 mg
Choline citrate (35 mg choline)—100 mg
Dimethylglycine HCl—100 mg
and the second formulation comprises:
Quercetin—500 mg
L-tyrosine—800 mg
Calcium ascorbate (160 mg vitamin C) 200 mg
Magnesium aspartate (40 mg magnesium)—200 mg
Calcium citrate (44 mg calcium)—200 mg
Proanthocyanidins—100 mg
Copper sebacate (4 mg copper)—20 mg
Folic acid—400 mcg.

10. The method according to claim 6 wherein the first formulation comprises:
Magnesium aspartate (220 mg magnesium)—1,100 mg
Dextrose, anhydrous—500 mg
L-5-hydroxytryptophan—180 mg
Calcium ascorbate (140 mg vitamin C)—175 mg
Inositol hexanicotinate (78.6 mg of niacin)—100 mg
Pyridoxine HCl—170 mg
Choline citrate (35 mg choline)—100 mg
Dimethylglycine HCl—100 mg
and the second formulation comprises:
Quercetin—500 mg
L-tyrosine—800 mg
Calcium ascorbate (160 mg vitamin C)—200 mg
Magnesium aspartate (40 mg magnesium)—200 mg
Calcium citrate (44 mg calcium)—200 mg
Proanthocyanidins—100 mg
Copper sebacate (4 mg copper)—20 mg
Folic acid—400 mcg.

11. The method according to claim 5 wherein the first formulation comprises:
Magnesium aspartate (220 mg magnesium)—1,100 mg
Dextrose, anhydrous—500 mg
Tryptophan—1,000 mg
Calcium ascorbate (140 mg vitamin C)—175 mg
Inositol hexanicotinate (132.6 mg of niacin)—170 mg
Pyridoxine HCl—170 mg
Choline citrate (35 mg choline)—100 mg
Dimethylglycine HCl—100 mg
and the second formulation comprises:
Quercetin—500 mg
L-tyrosine—800 mg
Calcium ascorbate (160 mg vitamin C)—200 mg
Magnesium aspartate (40 mg magnesium)—200 mg
Calcium citrate (44 mg calcium)—200 mg
Proanthocyanidins—100 mg
Copper sebacate (4 mg copper)—20 mg
Folic acid—400 mcg.

12. The method according to claim 6 wherein the first formulation comprises:
Magnesium aspartate (220 mg magnesium)—1,100 mg
Dextrose, anhydrous—500 mg
Tryptophan—1,000 mg
Calcium ascorbate (140 mg vitamin C)—175 mg
Inositol hexanicotinate (132.6 mg of niacin)—170 mg
Pyridoxine HCl—170 mg
Choline citrate (35 mg choline)—100 mg
Dimethylglycine HCl—100 mg
and the second formulation comprises:
Quercetin—500 mg
L-tyrosine—800 mg
Calcium ascorbate (160 mg vitamin C)—200 mg
Magnesium aspartate (40 mg magnesium)—200 mg
Calcium citrate (44 mg calcium)—200 mg
Proanthocyanidins—100 mg
Copper sebacate (4 mg copper)—20 mg
Folic acid—400 mcg.

13. The method according to claim 5 wherein the first formulation comprises:
Fructose—4,400 mg
Corn starch—3,500 mg
L-tryptophan—900 mg
Calcium ascorbate (200 mg of vitamin C)—250 mg
Inositol hexanicotinate (156 mg of niacin)—200 mg
Pyridoxine HCL—200 mg
and the second formulation comprises:
Quercetin—500 mg
L-tyrosine—800 mg
Calcium ascorbate (160 mg vitamin C)—200 mg
Magnesium aspartate (40 mg magnesium)—200 mg
Calcium citrate (44 mg calcium)—200 mg
Proanthocyanidins (grape seed extract)—100 mg
Copper sebacate (4 mg copper)—20 mg
Folic acid—400 mcg.

14. The method according to claim 6 wherein the first formulation comprises:
Fructose—4,400 mg
Corn starch—3,500 mg
L-tryptophan—900 mg
Calcium ascorbate (200 mg of vitamin C)—250 mg
Inositol hexanicotinate (156 mg of niacin)—200 mg
Pyridoxine HCL—200 mg
and the second formulation comprises:
Quercetin—500 mg
L-tyrosine—800 mg
Calcium ascorbate (160 mg vitamin C)—200 mg
Magnesium aspartate (40 mg magnesium)—200 mg
Calcium citrate (44 mg calcium)—200 mg
Proanthocyanidins—100 mg
Copper sebacate (4 mg copper)—20 mg
Folic acid—400 mcg.

15. A daily supplement for administering to a patient subject to migraine headaches, said daily supplement comprising a first and second formulation to increase brain levels of serotonin and norepinephrine in the patient, the said first formulation comprising:
L-tryptophan or L-5-hydroxytryptophan,
a methyl donor source,
a choline source,
a niacin source,
a carbohydrate, and
vitamin B6 and the second formulation comprising:
   L-tyrosine,
   a vitamin C source, and
   a copper source
and wherein one or more of folic acid, a bioflavanoid, proanthocyanidis, a source of calcium and a source of magnesium are present in at least one of said first and second formulations.

16. The daily supplement according to claim 15 wherein the first formulation comprises:
   Magnesium aspartate (220 mg magnesium)—1,100 mg
   Dextrose, anhydrous—500 mg
   L-5-hydroxytryptophan—180 mg
   Calcium ascorbate (140 mg vitamin C)—175 mg
   Inositol hexanicotinate (132.6 mg of niacin)—170 mg
   Pyridoxine HCl—170 mg
   Choline citrate (35 mg choline)—100 mg
   Dimethylglycine HCl—100 mg
and the second formulation comprises:
   Quercetin—500 mg
   L-tyrosine—800 mg
   Calcium ascorbate (160 mg vitamin C)—200 mg
   Magnesium aspartate (40 mg magnesium)—200 mg
   Calcium citrate (44 mg calcium)—200 mg
   Proanthocyanidins—100 mg
   Copper sebacate (4 mg copper)—20 mg
   Folic acid—400 mcg.

17. The daily supplement according to claim 15 wherein the first formulation comprises:
   Magnesium aspartate (220 mg magnesium)—1,100 mg
   Dextrose, anhydrous—500 mg
   Tryptophan—1,100 mg
   Calcium ascorbate (140 mg vitamin C)—175 mg
   Inositol hexanicotinate (132.6 mg of niacin)—170 mg
   Pyridoxine HCl—170 mg
   Choline citrate (35 mg choline)—100 mg
   Dimethylglycine HCl—100 mg
and the second formulation comprises:
   Quercetin—500 mg
   L-tyrosine—800 mg
   Calcium ascorbate (160 mg vitamin C)—200 mg
   Magnesium aspartate (40 mg magnesium)—200 mg
   Calcium citrate (44 mg calcium)—200 mg
   Proanthocyanidins—100 mg
   Copper sebacate (4 mg copper)—20 mg
   Folic acid—400 mcg.

18. The daily supplement according to claim 15 wherein the first formulation comprises:
   Fructose—4,400 mg
   Corn starch—3,500 mg
   L-tryptophan—900 mg
   Calcium ascorbate (200 mg of vitamin C)—250 mg
   Inositol hexanicotinate (156 mg of niacin)—200 mg
   Pyridoxine HCL—200 mg
and the second formulation comprises:
   Quercetin—500 mg
   L-tyrosine—800 mg
   Calcium ascorbate (160 mg vitamin C)—200 mg
   Magnesium aspartate (40 mg magnesium)—200 mg
   Calcium citrate (44 mg calcium)—200 mg
   Proanthocyanidins—100 mg
   Copper sebacate—4 mg
   Folic acid 400 mcg.

19. The daily supplement according to claim 15 wherein the first formulation comprises three capsules of the components of said first formulation and the second formulation comprises three capsules of the components of said second formulation.

20. The daily supplement according to claim 16 wherein the first formulation comprises three capsules of the components of said first formulation and the second formulation comprises three capsules of the components of said second formulation.

21. The daily supplement according to claim 17 wherein the first formulation comprises three capsules of the components of said first formulation and the second formulation comprises three capsules of the components of said second formulation.

22. The daily supplement according to claim 18 wherein the first formulation comprises three capsules of the components of said first formulation and the second formulation comprises three capsules of the components of said second formulation.

* * * * *